US007845355B2

(12) United States Patent
Moench et al.

(10) Patent No.: US 7,845,355 B2
(45) Date of Patent: Dec. 7, 2010

(54) INTRAVAGINAL DEVICE WITH IMPROVED RIM DESIGNS AND METHODS OF MAKING SAME

(75) Inventors: Thomas R. Moench, Baltimore, MD (US); Richard A. Cone, Baltimore, MD (US); Randy Wills, Florence, MT (US)

(73) Assignees: Reprotect, Inc., Baltimore, MD (US); The Johns Hopkins University, Baltimore, MD (US)

( * ) Notice: Subject to any disclaimer, the term of this patent is extended or adjusted under 35 U.S.C. 154(b) by 1233 days.

(21) Appl. No.: 11/133,472

(22) Filed: May 19, 2005

(65) Prior Publication Data
US 2006/0260619 A1 Nov. 23, 2006

(51) Int. Cl.
*A61F 6/06* (2006.01)
(52) U.S. Cl. ...................................... 128/833
(58) Field of Classification Search ................. 128/833, 128/834, 837, 838, 839, 841
See application file for complete search history.

(56) References Cited

U.S. PATENT DOCUMENTS

| 2,697,057 | A | | 12/1954 | Senger et al. |
| 3,216,422 | A | | 11/1965 | Steiger et al. |
| 4,093,490 | A | | 6/1978 | Ziets et al. |
| 4,684,490 | A | | 8/1987 | Taller et al. |
| 4,785,804 | A | * | 11/1988 | Tlapek et al. ............... 128/841 |
| 5,295,984 | A | | 3/1994 | Contente et al. |
| 5,554,673 | A | | 9/1996 | Shah |
| 5,571,567 | A | | 11/1996 | Shah |
| 6,216,697 | B1 | | 4/2001 | Moench et al. |
| 6,241,846 | B1 | | 6/2001 | Contente et al. |

(Continued)

FOREIGN PATENT DOCUMENTS

EP 0006609 1/1980

(Continued)

OTHER PUBLICATIONS

Boskey ER, Moench TR, Hees PS, Cone RA. A self-sampling method to obtain large volumes of undiluted cervicovaginal secretions. Sexually Transmitted Diseases. 2003; 30:107-9.

(Continued)

*Primary Examiner*—Patricia M Bianco
*Assistant Examiner*—Camtu T Nguyen
(74) *Attorney, Agent, or Firm*—Whyte Hirschboeck Dudek SC

(57) ABSTRACT

The present invention provides improved rim designs for diaphragms or any similar intravaginal device and methods for producing same. The rim designs of the present invention improve, among other characteristics of the rim, structural durability, manufacturability, ease of insertion, comfort in use, and ease of removal of intravaginal devices. These designs incorporate one or more recesses in the inner portion of a rim piece that provide an attachment site for a separate dome piece. Attachment within a recess shields the exposed outer edge of the dome material from contact with epithelial surfaces and improves comfort and safety. In certain embodiments of the invention, a thinned inner portion of the rim serves as a handle that can be easily grasped by a finger to remove the device from the vagina. These devices are useful in providing a protective cervical barrier for contraception and disease prevention, to deliver beneficial agents, and as a means to collect and remove substances from the vagina.

22 Claims, 14 Drawing Sheets

U.S. PATENT DOCUMENTS

| | | |
|---|---|---|
| 6,264,638 B1 | 7/2001 | Contente |
| 6,474,338 B2 | 11/2002 | Moench et al. |
| 6,796,973 B1 | 9/2004 | Contente et al. |
| 2003/0060785 A1 | 3/2003 | Lavean et al. |
| 2004/0020494 A1 | 2/2004 | Burpee |

FOREIGN PATENT DOCUMENTS

| | | |
|---|---|---|
| EP | 0134671 | 3/1985 |
| GB | 2 218 666 A | 11/1989 |

OTHER PUBLICATIONS

Martino JI, Youngpairoj S, Vermund SH. "Vaginal douching: personal practices and public policies". *Journal of Womens Health* (Larchmont). Nov. 2004;13(9):1048-65.

International Search Report of corresponding PCT Application No. PCT/US06/19462, dated Jul. 26, 2007, 2 pages.

* cited by examiner

INTRAVAGINAL DEVICE WITH IMPROVED RIM DESIGNS AND METHODS OF MAKING SAME

BACKGROUND

Intravaginal devices such as diaphragms and other cervical barrier devices are useful for contraception and disease prevention. Such devices can also be used for collecting menstrual discharge, collection of vaginal samples, or to deliver therapies. A typical design of an intravaginal device consists of a flexible rim surrounding a hemispheric-shaped dome, often manufactured using a mold that simultaneously forms both the rim and the dome. The dome provides barrier, collection, and/or drug delivery functions, whereas the rim holds and supports the dome during insertion and during wear within the vagina.

Various designs and methods of construction are known. One of the most common designs includes a metal spring in the rim of the device to provide elastic force that restores the rim to its expanded configuration after being compressed during vaginal insertion. The spring is incorporated into the rim by a molding process that simultaneously creates the dome and covers the spring with a continuous and unbroken layer of elastomer. Other designs use rims that are entirely elastomeric without metal springs. Although molding the rim and dome as a single piece creates devices with smooth surfaces that provide comfort in use, the domes created by this method are relatively thick. This is because it is difficult to mold parts having a relatively large surface area as a thin piece. The dome portion must remain relatively thick to allow proper filling of the mold because the injected polymer must flow a long distance through a narrow mold cavity.

It is advantageous, however, for an intravaginal device to have a thin dome. Thin domes are compact when compressed for insertion, and they can be made very soft and compliant. To create a thin dome requires methods that employ assembly of the device from separate dome and rim pieces. The film piece is attached to the rim where it can be further shaped and expanded by thermoforming (softening by heating, and drawing by vacuum into a mold shaped to the desired final dome shape), which further reduces the dome thickness. In addition, the device assembled from separate pieces allows a single rim design to be used with multiple different dome shapes such as the roughly hemispheric shape of conventional diaphragms, or other dome shapes.

A significant disadvantage of diaphragms and similar devices assembled from a separate dome piece and a separate rim piece that has not been recognized or overcome in the prior art is the exposure of an unprotected and potentially harsh outer edge of the dome material upon attaching the dome to the rim. FIG. 1, for example, illustrates a common rim design in the prior art having a circular cross-section with a width 18 less than or equal to its height 20. As illustrated in FIG. 1, the dome piece 10 is positioned for attachment at a typical attachment site 16 on the upper surface of the rim 12. When attached, the dome piece edge 14 is disadvantageously exposed and unprotected.

A sharp edge may be created at an outer edge of a dome piece if the dome film is cut to shape before attachment. A rough or sharp edge just outside the attachment site can also be created with a known alternative assembly method of simultaneously attaching a plurality of domes to the top of a plurality of rims, employing a multi-headed welding tool. An oversized uncut piece of dome film is stretched over the multi-headed welding tool. The multi-headed welding tool presses through the sheet of dome film onto the rims, and the web of film outside the perimeter of the welding tool softens to form a weld line. The waste web is subsequently pulled free from the heat-softened weld line. Although precautions can be taken during manufacture to reduce roughness of the exposed edge, for example, by adding subsequent smoothing steps or shaping the welding tool to minimize residual roughness, these extra steps add cost and complexity, and may be only partially effective.

The outer edge of the attached film may be sufficiently rough or sharp to irritate or injure the vagina during insertion or wear, and irritate or injure the penis during sexual intercourse. Even if the weld-edge roughness is sufficiently minimal that detectable injury does not result, any roughness felt during insertion, wear or intercourse is disadvantageous.

Another disadvantage of attaching the dome to an unprotected surface of the rim is the resulting exposure of the edge of the dome to forces that may pull it loose from the rim. During insertion or with movement during wear, an exposed edge of the dome material may rub against epithelial surfaces, and, with sufficient purchase of the epithelium on the edge, may be pulled loose from the rim, especially if a local weakness in the attachment bond is present. Movement during intercourse may also contribute to detachment of the dome material due to traction on an exposed dome edge. Any detachment along the attachment bond or any separation of the dome material from the rim can compromise barrier function of the device. Even partial detachment that does not compromise the barrier function can create a crevice or flap between the dome and rim that is difficult to clean and reduces the suitability of the device to function as a re-usable device.

Also, diaphragms and similar devices may be difficult to grasp for positioning within or removal from the vagina. To remove a typical diaphragm, a user must grasp the device at the rim, generally by pushing the dome material up inside the perimeter of the rim to allow the fingertip to curve around the top of the rim from the inside, and then by pulling the rim downward and out of the vagina. Grasping the upper surface of the rim can be difficult since the dome material tends to interfere with access to this portion of the rim, and since the grasping finger must traverse the entire height of the rim to gain purchase on its upper surface.

SUMMARY

The present invention provides rim designs for diaphragms and similar intravaginal devices, which improve their manufacturability, ease of insertion, comfort in use, and ease of removal. These designs incorporate one or more recesses in the inner portion of a rim piece that provide a protected site on the rim for dome attachment, where a separate dome piece is positioned and attached. Attachment within a recess shields the potentially sharp or rough outer edge of the dome material from contact with epithelial surfaces, and improves comfort and safety. Incorporating one or more recesses into the inner portion of the rim also reduces the tendency of the rim to twist during compression, and thus improves its stability during handling before and during insertion. In certain embodiments of the invention, a thinned inner portion of the rim serves as a handle that can be easily grasped by a finger used to position the device and to remove the device from the vagina.

In an embodiment of the present invention, an intravaginal device is provided with a rim piece including an inner portion. The rim piece includes at least one recess associated with the inner portion of the rim piece. The device also includes a dome piece having a thickness. The depth of the recess is at least as great as the thickness of the dome piece. The dome piece is operably attached to the rim piece within a recess of the inner portion of the rim piece.

In an embodiment, a cross-sectional width of the rim piece of the device is greater than or equal to a cross-sectional height of the rim piece.

In an embodiment, a plurality of recesses are associated with the inner portion of the rim piece.

In an embodiment, the depth of at least one of the recesses is equal to the depth of at least one of the other recess.

In an embodiment, the depth of at least one recess is different than the depth of at least one other recess.

In an embodiment, the recesses associated with the inner portion of the rim piece define a thickness of the inner portion, wherein the thickness approaches the thickness of the dome piece.

In an embodiment, the dome piece is attached to the rim piece at a substantially central position between a top portion and a bottom portion of the rim piece.

In an embodiment, the dome piece is attached to the rim piece at a position away from a central position between a top portion and a bottom portion of the rim piece.

In an embodiment, the thickness of the inner portion of the rim piece is between about 1 and about 0.01 millimeters.

In an embodiment, the inner portion of the rim piece is adapted to function as a handle to position the device within a vagina and remove the device from the vagina.

In an embodiment, an outer portion of the rim piece includes at least one outwardly projecting circumferential bead.

In an embodiment, an outer portion of the rim piece includes at least one circumferential groove.

In an embodiment, the dome piece is attached to the rim piece by an attachment method selected from the group consisting of: thermowelding, ultrasonic welding, radiofrequency welding, solvent welding, and adhesive attachment.

In an embodiment, a method of forming an elastomeric dome piece of the intravaginal device of the claimed invention is provided. The method includes, after attaching said dome piece to said rim piece, softening the dome piece by heating and drawing the dome piece by vacuum into a mold. The mold is shaped to a desired dome piece shape.

In another embodiment, a method of producing and attaching an elastomeric dome of an intravaginal device to a rim of the device is provided. The method includes forming a rim having an inner portion. The inner portion includes at least one recess. The method also includes placing the rim over a mandrel so that the inner portion of the rim contacts the mandrel. The method further includes applying a polymer and solvent mixture to the rim and mandrel. The method further includes allowing the mixture to coat the mandrel such that the mixture contacts the inner portion of the rim. The method further includes allowing the solvent to evaporate.

In an embodiment, the method of applying the polymer and solvent mixture to the rim and mandrel includes spraying the polymer and solvent mixture to the rim and mandrel.

In a further embodiment, a method of removing substances from the vagina is provided. The method includes operably positioning in the vagina of an individual in need thereof an intravaginal device. The device includes a rim piece including an inner portion and an outer portion and a dome piece having a thickness. The rim piece includes at least one recess associated with the inner portion. The recess includes a depth wherein the depth of the recess is at least as great as the thickness of the flexible dome piece. The dome piece is operably attached to the rim piece within the recess of the inner portion of the rim piece. The method also includes removing the intravaginal device from the vagina.

In an embodiment, the rim piece includes at least two recesses. The recesses oppose one another to define a dome attachment site at a substantially central position along the inner portion of the rim piece.

In yet another embodiment, a method of preparing an intravaginal device is provided. The method includes providing a rim piece including an inner portion. The rim piece includes at least a first recess and a second recess associated with the inner portion. The method also includes placing the rim piece on a rim support. The rim support is positioned within the first recess of the rim piece. The method further includes positioning a dome piece within the second recess of the rim piece and attaching the dome piece to the inner portion of the rim piece.

In yet a further embodiment, a method of preparing an intravaginal device is provided. The method includes placing dome material on a holding surface and providing vacuum pressure from the holding surface that is sufficient to maintain the dome material in a position on the holding surface. The method also includes cutting the dome material to form a dome piece. The method further includes providing a rim piece including an inner portion. The rim piece includes at least a first recess and a second recess associated with the inner portion. The method additionally includes placing the rim piece on a rim support. The rim support is positioned within the first recess of the rim piece. The method includes positioning the dome piece on the holding surface within the second recess of the rim piece and attaching the dome piece to the inner portion of the rim piece.

In an embodiment, the method includes transferring the dome piece from the holding surface to the rim piece. Transferring the dome piece includes at least reducing vacuum pressure from the holding surface.

In an embodiment, the method includes transferring the dome piece from the holding surface to the rim piece. Transferring the dome piece includes providing vacuum pressure from the rim support sufficient to substantially hold the dome piece within the second recess of the rim piece.

In an embodiment, the method includes providing vacuum pressure from the rim support sufficient to maintain the rim piece in a position on said rim support.

It is an advantage of the present invention to provide a device with an improved rim design.

Another advantage of the present invention is to provide a protected attachment site for the edge of the dome piece.

Yet another advantage of the present invention is to provide a device with a rim having a dome attachment site located substantially symmetrically between the top and bottom edge of the rim.

A further advantage of the present invention is to provide a device that is easier to remove.

An additional advantage of the present invention is to provide a device with a rim shape that aids in the retention of beneficial agents during insertion.

Yet another advantage of the present invention is to provide a device that can collect and remove materials from the vagina.

Yet an additional advantage of the present invention is to provide a device that more effectively cleanses the vagina of secretions and prior doses of medication, thus preventing accumulation and subsequent vaginal discharge.

Yet a further advantage of the present invention is to provide a method for producing intravaginal devices.

Yet another advantage of the present invention is to provide a device that is less prone to twisting when compressed for insertion.

Additional features and advantages of the present invention are described in, and will be apparent from, the following Detailed Description and the figures.

DETAILED DESCRIPTION

The present invention relates to intravaginal devices. In particular, the present invention relates to an intravaginal device including a rim piece and a dome piece. The rim includes at least one recess on its inner surface into which the outer edge of the dome piece is placed and attached. Positioning the edge of the dome piece in this recess prevents the potentially sharp or rough outer edge of the dome piece from contacting either the vaginal or penile epithelium and protects the edge of the dome from being peeled away from the rim as may occur if the dome piece was attached on an exposed surface of the rim. As discussed above, FIG. 1 illustrates a typical design of the prior art where a dome piece edge 14 is disadvantageously exposed when attached on the upper surface of a rim 12 with a circular cross-section having a width 18 equal to its height 20.

Figure 2:
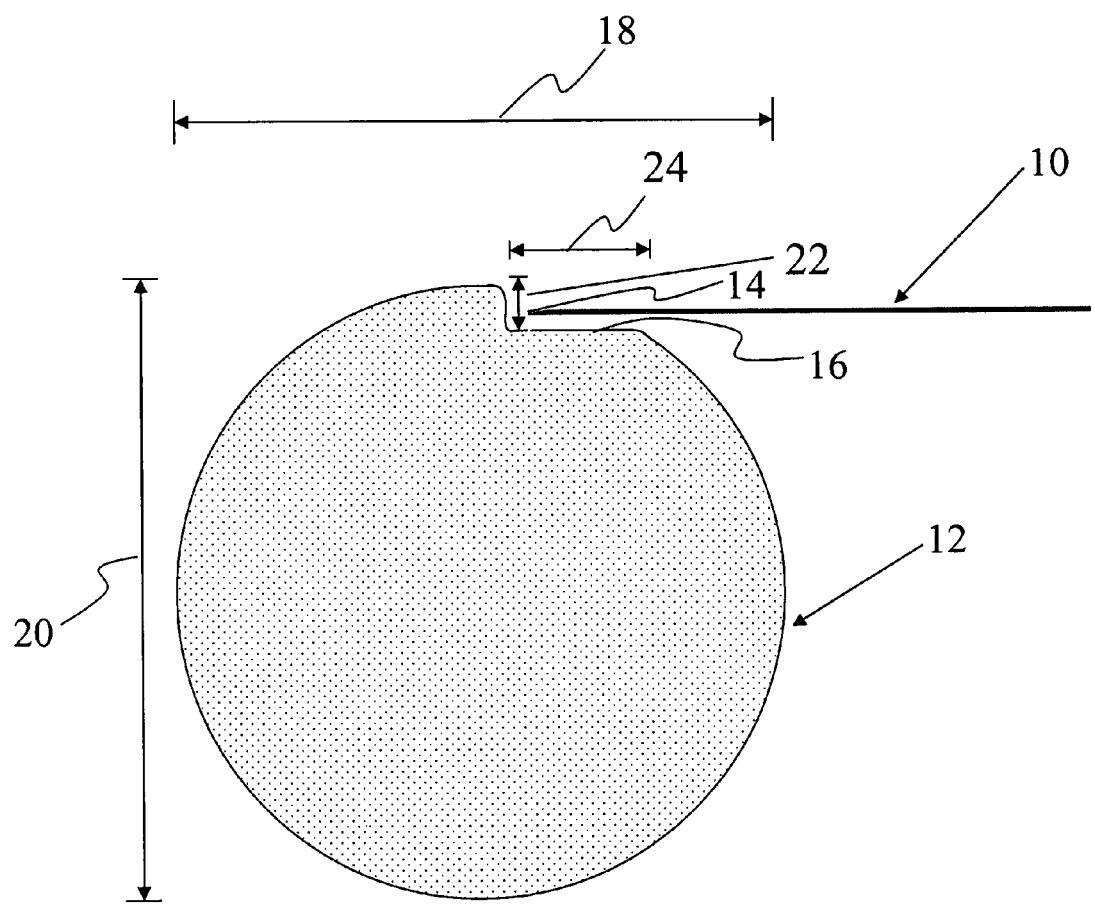
FIG. 2 is a cross-section of a portion of a rim and dome piece of an intravaginal device, with the dome piece positioned above the rim in preparation for attachment within a recess in the rim of one embodiment of the present invention.

Referring now to the remaining drawings, as illustrated in FIG. 2, the intravaginal device of one embodiment of the present invention includes a rim 12 having a substantially round cross-section. The rim 12 may include a recess associated with an inner aspect of the rim. The recess may be located along any portion of the inner aspect of the rim including a peripheral aspect of the rim as illustrated in FIG. 2. The recess may include a depth 22 and a width 24. The recess width 24 (measured in the horizontal dimension) may be at least sufficient to define an attachment site 16 adapted to receive the outer edge 14 of a dome piece 10. The recess depth 22 (measured in the vertical dimension) may be at least as great as the thickness of the dome piece 10, to effectively shield the edge 14 from contact once attached within the recess.

In one embodiment, the depth 22 of the recess into which the dome piece 10 is positioned and attached is substantially greater than the thickness of the dome piece. Among other advantages, this feature has the advantage of partially shielding the dome attachment site from the full extent of heating it would otherwise experience during subsequent shaping of the dome piece by thermoforming (see below). This shielding is due to the location of the attachment site 16 in the recess, which, if sufficiently deep, creates a shadowing or protective effect, reducing the heating received from a wide thermal source that may be used to soften the dome piece in preparation for shaping. When using a wide heat source as is used in manufacturing where multiple devices are thermoformed at the same time, only the portion of the heat source directly above a recessed dome will radiate heat to the edge of the recess, the location of the attachment site. Reducing additional heating to the attachment site 16 after the attachment step is advantageous, since cumulative "heat-history" can reduce polymer resilience, can induce undesirable yellowing, and can reduce the strength and integrity of the bond between dome piece 10 and rim piece 12.

The recess width 24 is preferably sufficient to provide a secure and reliable attachment site 16 for the dome piece 10 to the rim 12. In one embodiment, at least one recess defines a substantially horizontal surface associated with the inner portion of the rim. The width of the recess 24 (measured in the horizontal dimension) is advantageously between about 1 and about 5 mm, more preferably between about 2 and about 4 mm in width.

Figure 12A:
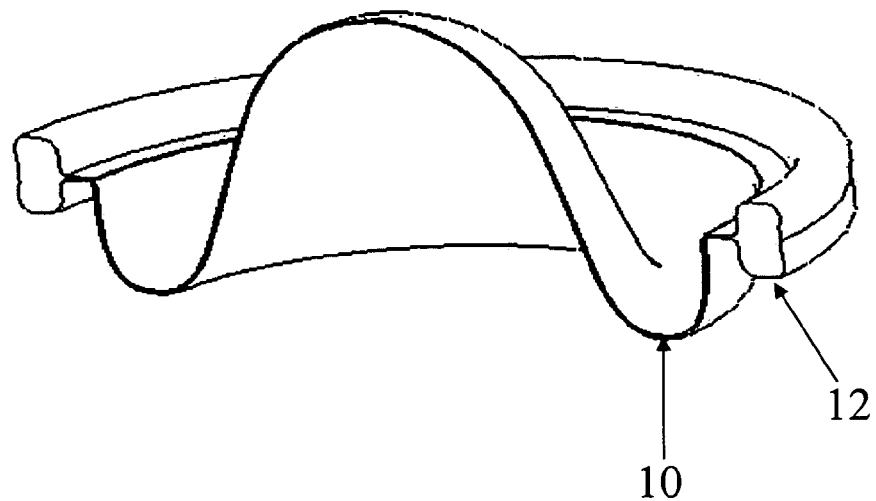
FIG. 12A is a cross-sectional perspective view of an intravaginal device of one embodiment of the present invention with an attached and formed dome.
Figure 12B:
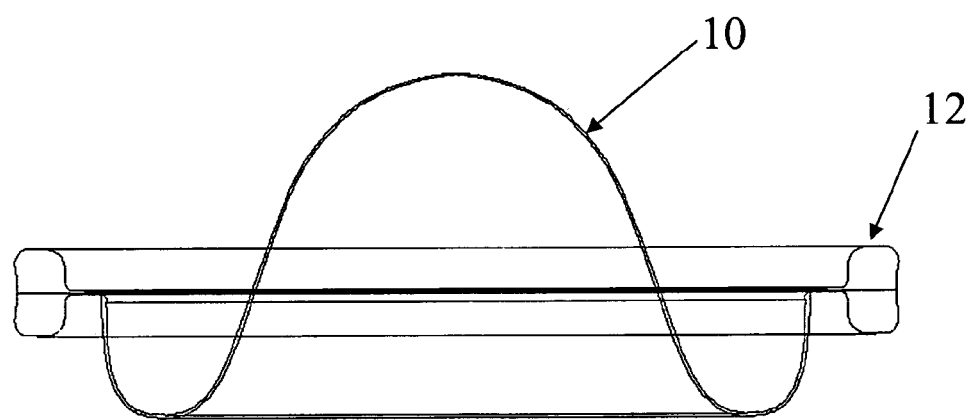
FIG. 12B is a cross-sectional view of an intravaginal device of one embodiment of the present invention with an attached and formed dome.

A substantial recess width 24 associated with the rim is also beneficial in holding certain preferred dome designs in place during compression for insertion. For example, the sombrero-shaped dome described in U.S. Pat. No. 6,474,338 may be used with any of the rim designs of the present invention including, as illustrated in FIG. 12, the rim design illustrated in FIG. 5. The upwardly projecting central portion of the sombrero-shaped dome, together with any added beneficial agent, is pulled down by gravity as the device is held in preparation for the insertion step. The dome and/or any applied beneficial agent can fall through the plane of the rim defeating the proper function of this dome design. A generous width of the recess of the rim helps prevent this by extending across the gap between opposing sections of the compressed or partially compressed rim.

Non-circular cross-section rim designs are used in existing intravaginal devices to reduce the bowing and twisting associated with circular cross-section rim designs during compression of the device in preparation for insertion. Formation of an awkward shape such as a "twisted figure-8" configuration complicates proper insertion of the intravaginal device. Metal-free, fully elastomeric rims with round cross-sections are even more prone to bowing and twisting.

Figure 3:
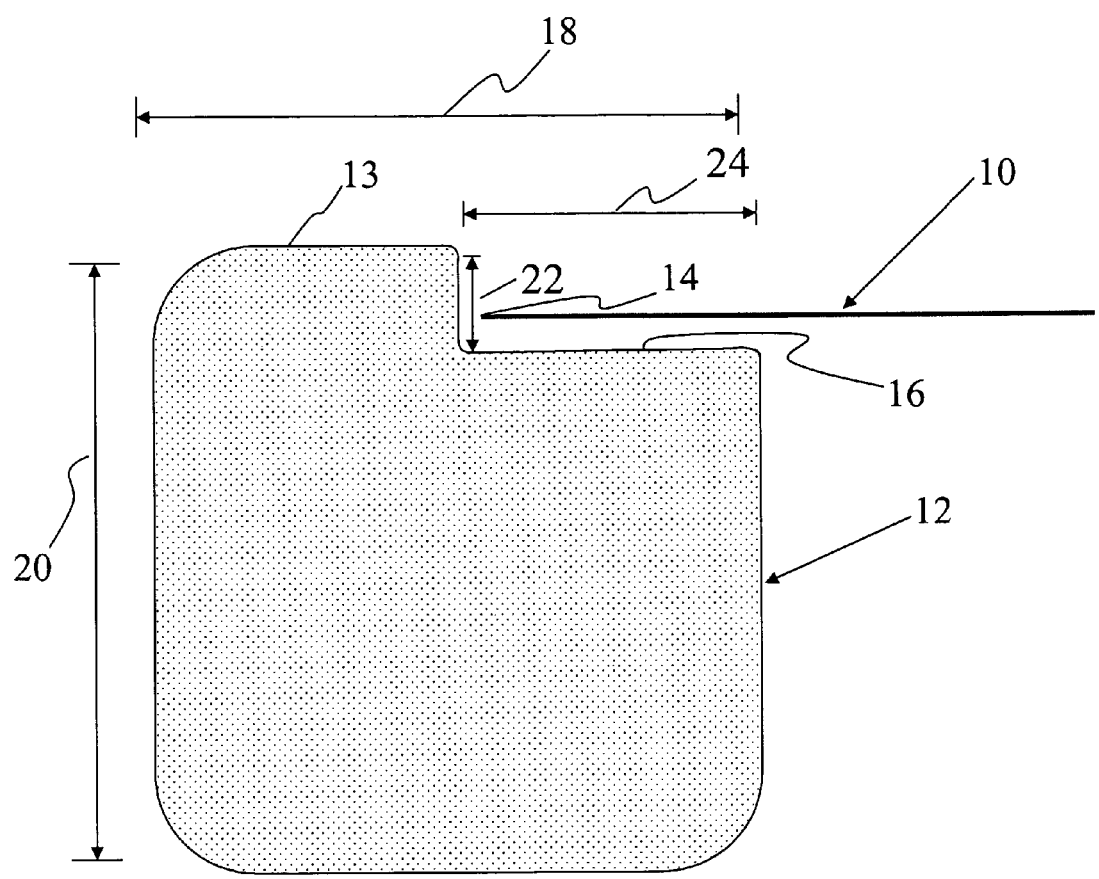
FIG. 3 is a cross-section of a portion of a rim and dome piece of an intravaginal device illustrating attachment of the dome piece within a recess in the rim of one embodiment of the present invention.

In one embodiment, the cross-sectional width of the rim 18 is greater than or equal to the cross-sectional height 20 of the rim. FIG. 3, for example, illustrates another embodiment of the rim 12 of the present invention having a substantially non-circular cross-section. The embodiment illustrated in FIG. 3 includes a rim having a cross-sectional width 18 greater than or equal to a cross-sectional height 20 of the rim forming in this case a substantially square cross-section rim. Similar to the embodiment illustrated in FIG. 2, the embodiment illustrated in FIG. 3 includes a recess in the upper surface of its inner portion defining an attachment site 16 adapted to receive the outer edge 14 of a dome piece 10.

The rim must have substantial width in order to provide a sufficiently ample attachment site along the inner portion of the rim for assembly of the dome piece to the rim piece while retaining sufficient strength and resiliency in the outer portion of the rim to create an adequate outward holding force to hold the rim in proper position in the vagina. In one embodiment, the width of the rim is advantageously made less than about 10 mm, and more advantageously between about 5 and about 8 mm. In one embodiment, the upper, non-recessed outer portion of the rim is sufficient to retract epithelial surfaces away from the potentially rough edge 14 of the dome material 10. An ample total rim width is also advantageous to provide a wide enough inner portion to be easily grasped by the retrieving finger. The described range of widths is also advantageous in order to avoid the thinned inner portion of the rim being excessively wide and thereby being prone to press against the cervix, which will lie within the perimeter of the rim.

At the same time, there are practical upper limits on rim height 20. If the rim height is excessive, it may extend downward from behind the pubic bone during wear, and be obstructive during intercourse. To this end, the height of the rim is advantageously made less than about 10 mm, and more advantageously, between about 5 and about 8 mm. Thus, the need for a substantial rim width 18, and the limits on the rim height 20, make it advantageous for the rim width 18 to be greater than or equal to the rim height 20.

In one embodiment, the dome piece is attached to at least the substantially horizontal surface of an inner recessed portion of the rim. The dome piece may also be attached to at least a substantially vertical and a substantially horizontal surface of the inner recessed portion of the rim.

Figure 4:
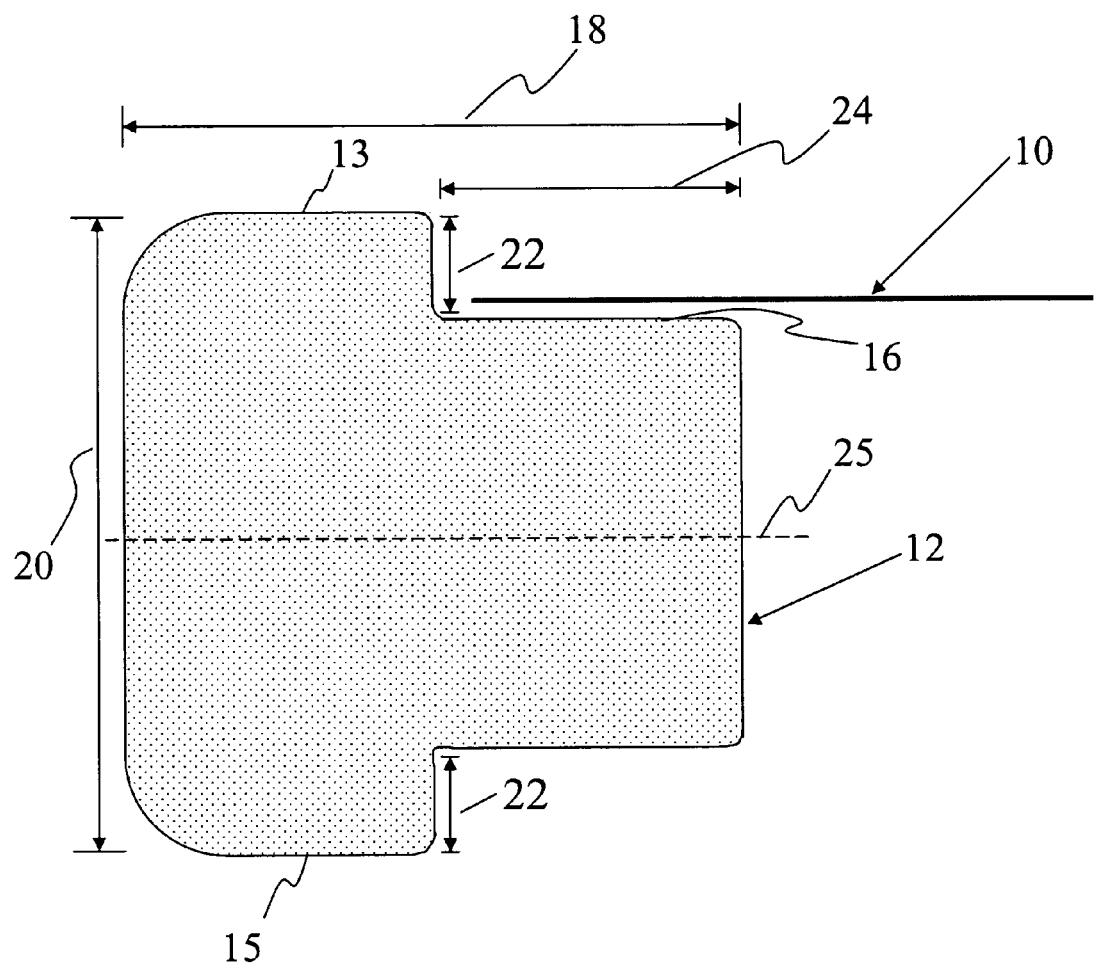
FIG. 4 is a cross-section of a portion of a rim and dome piece of an intravaginal device illustrating attachment of the dome piece within a recess in the rim of one embodiment of the present invention.

In another embodiment, illustrated in FIG. 4, a rim 12 includes more than one recess associated with the inner portion of a rim. In one embodiment, the rim includes multiple recesses. A recess may be associated with a top portion 13 of the rim and a recess may be associated with a bottom portion 15 of the rim. The recesses may have substantially equivalent dimensions and/or be positioned symmetrically along the inner portion of the rim on either side of an approximate vertical center 25 of the rim. It should be appreciated that symmetry in design is advantageous during manufacture and use of intravaginal devices. For example, a symmetrical rim design may not require an "up-down" orientation step during manufacture of the rim. Avoiding an orientation step is a significant advantage during high-volume manufacturing.

An additional benefit of providing one or more recesses in the inner portion of the rim is a reduction in the tendency of the rim to twist awkwardly when compressed for insertion.

Figure 5:
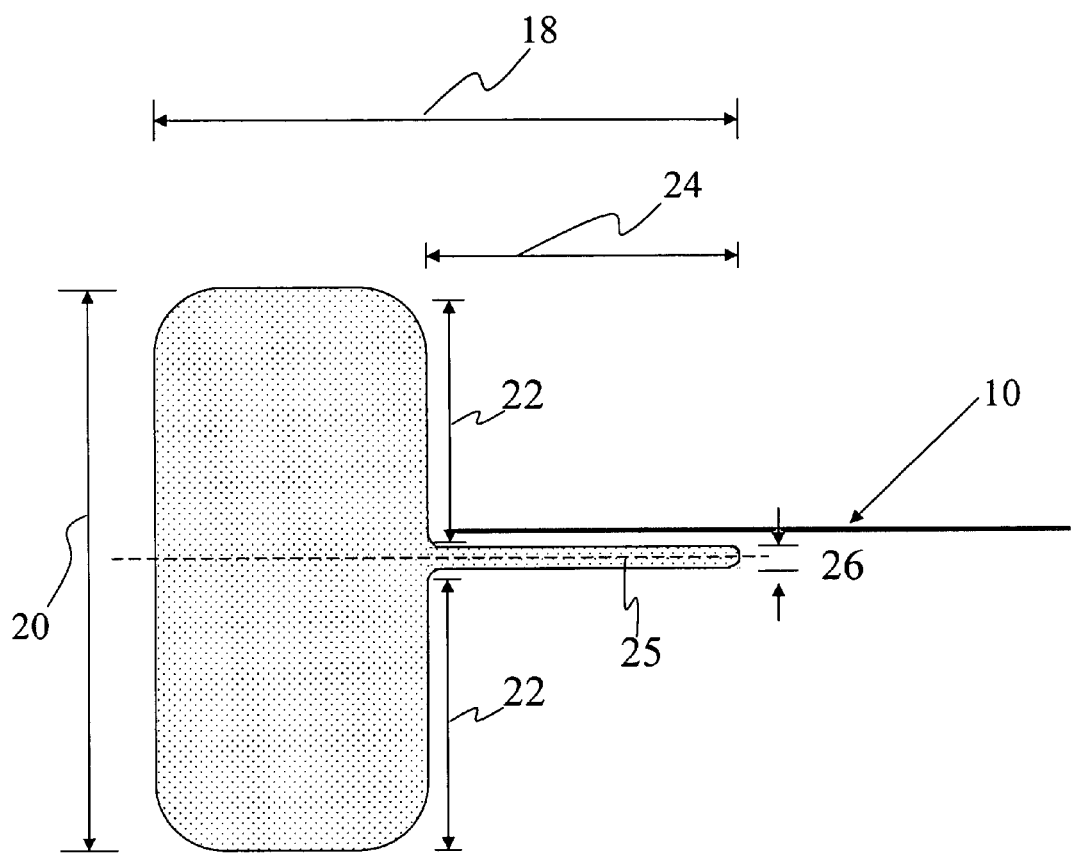
FIG. 5 is a cross-section of a portion of a rim and dome piece of an intravaginal device illustrating attachment of the dome piece within a recess in the rim of one embodiment of the present invention.
Figure 6:
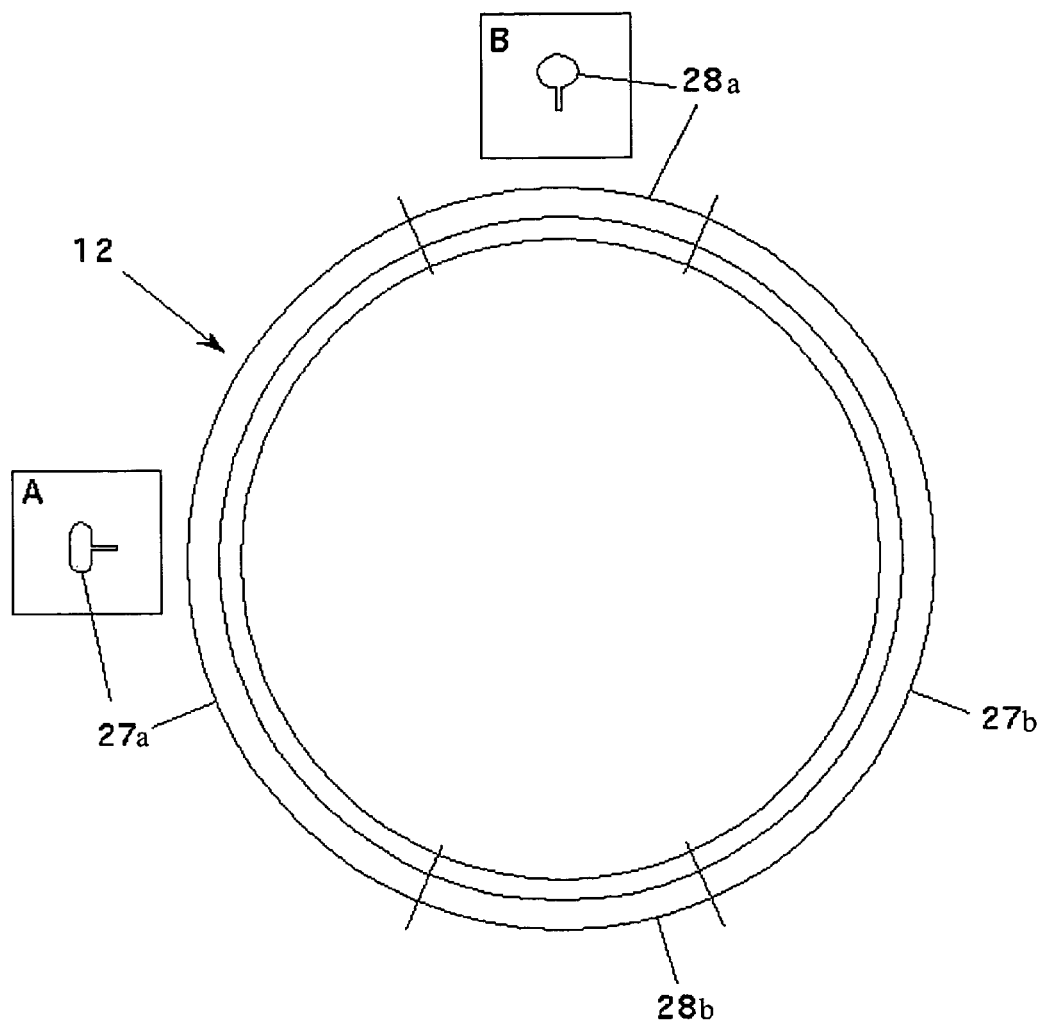
FIG. 6 is a top down view of a rim of one embodiment of the present invention that is divided into segments demarcated by radial dashed lines with different cross-sectional profiles that are shown in insets A and B.

In an embodiment illustrated in FIG. 5, not only the rim, but also the entire device may be made essentially symmetrical in regard to its up-down orientation. In the embodiment illustrated in FIG. 5 the cross-section of the rim of the intravaginal device is substantially symmetrical above and below an approximate center 25 of the rim. In such an embodiment, the symmetrical recesses associated with the top portion 13 and bottom portion 15 of the rim are made sufficiently deep to locate the attachment site 16 to the inner portion of the rim at the approximate center 25 of the rim. In an embodiment having a compliant dome attached to the substantially central portion 25 of the inside of the rim, the dome can be deployed in either direction and, therefore, the device can be inserted without regard to up-down orientation. Thus, in the embodiment shown in FIG. 5, the device can be placed in the vagina with either surface pointing upward without the user having to manipulate the device into a correct "up-down" orientation.

As compared to the embodiments illustrated in FIGS. 2, 3 and 4, FIG. 5 further illustrates that, in an embodiment, the dimensions of the recess of the inner portion of the rim can vary. In the embodiment illustrated in FIG. 5, the recesses are sufficient to form a rim that is significantly more compliant along its inner portion than the rest of the rim. The dimensions of the recesses can be manipulated to form a rim that is not too thick along its inner portion, thus preventing the rim from having a stiff and sharp edge that can press against the cervix. In addition, the dimensions of the recesses may be manipulated to form a rim that is sufficiently thick along its inner portion to provide a strong and robust attachment site. Additionally, a portion of the rim that is too thin will also not be stiff enough to serve as a suitable handle (see below). Optimizing the compliance of the rim along its inner portion offers sufficient stiffness for the inner portion of the rim to be easily grasped and to function as a handle (see below) while being sufficiently compliant to prevent its inward facing edge from being a sharp and potentially damaging contact point with the cervix. Moreover, if the rim has an excessively thin portion, it may be difficult during fabrication of the rim to fill this portion in a mold or during extrusion molding through a die. To achieve appropriate softness or compliance in one embodiment, opposing recesses in the inner portion of the rim may advantageously define a rim having an inner portion thickness 26 of between about 1 and about 0.01 mm in the vertical dimension, and, more advantageously, between about 0.5 and about 0.1 mm in thickness. Thus the thickness of the inner portion can, in one embodiment, advantageously approach the thickness of the dome material (see below).

Being an intrinsic part of the rim, the inner portion of the rim may possess a stiffness-discontinuity with the dome material by virtue of the greater stiffness of the rim material. This stiffness-discontinuity at the junction of the dome and rim may allow this junction to serve as a handle. To this end, a further advantage of the design illustrated in FIG. 5 is that the inner portion of the rim can function as a handle that provides a significantly more favorable gripping site for the user to position and to remove the device. In such an embodiment, the inner portion of the rim is more easily grasped than the rims of prior designs. For example, to remove a device having a rim with a prior design, the user must direct a retrieving finger to generally reach inside the rim, all the way to the upper edge of the rim while pushing the dome out of the way to access the edge of the rim. Access to this area may be difficult with conventional diaphragms and similar intravaginal devices since their relatively thick and non-compliant domes can interfere with grasping the rim. In contrast, the thin dome material characteristic of some embodiments of the present invention can be less interfering, and the recessed inner portion of the rim designs of the present invention may enable the retrieving finger of the user to reach the inner portion of the rim at a point substantially below the upper edge of the rim with less need to move the dome material out of the way as is required with conventional diaphragms.

An additional advantage of the embodiments illustrated in FIGS. 5-11 having a substantially central attachment site, and hence takeoff point, of the dome includes an improved efficiency in collecting and removing secretions from the vagina and/or substances that have been applied to the vagina. To this end, in one embodiment, the devices of the present invention may be used as a vaginal cleansing system. This improved efficiency of removal of substances from the vagina is due, in part, to the substantially central, or minimally asymmetric (FIG. 7) attachment site, and, hence, takeoff point of the dome. In one embodiment, the configuration of the rim formed by opposing recesses associated with the inner portion of the rim can give the rim cross-section a substantial "T" shape that has been laid on its side, with the inner portion of the rim being the stem, and the outer portion of the rim being the arms of the "T". The arms of the "T" can serve the function of gentle scrapers or "squeegees", that, as the device is withdrawn from the vagina, cleanse the vaginal epithelium of adherent secretions, menstrual fluid, or applied substance on one or both sides of the device. As the device is pulled over the epithelium, the arms formed by the rim design of the present invention can efficiently wipe fluids off the vaginal walls, collect them within the perimeter of the rim, and substantially remove them from the vagina along with the device. Such an effective two-sided squeegee action may reduce the amount of discharge from the vagina after intercourse, or after application of medications.

Devices of the described embodiments thus can be used as a vaginal cleansing system, allowing effective cleansing without the multiple negative health outcomes associated with vaginal douching (Martino et al, 2004). More effective vaginal cleansing can be useful during or after menses, after sexual intercourse, or in the presence of vaginal discharge diseases. Prior designs of intravaginal devices, wherein the dome film is attached to an exposed edge of the rim, are disadvantageous in that an effective squeegee function may only be achieved, if at all, on the surface opposite the dome attachment. The surface with the dome attachment site will not effectively collect substances from the vaginal wall upon withdrawal of the device because the dome will prevent material from being gathered within the perimeter of the rim.

The rim design illustrated in FIG. 5 and other embodiments where the inner portion of the rim is substantially thinned is also far less susceptible to twisting or bowing upon compression of the device for insertion than round or even substantially square rim cross-sections. However, even the embodiments of rims having substantially thinned inner portions similar to the embodiment illustrated in FIG. 4 still have some tendency to twist. Accordingly, one embodiment includes a packaging system that holds the device in an oval shape until the device is removed from the package. Packaging the device in such a way results in substantial further reduction in the tendency of the device to twist when compressed for insertion.

It will be appreciated that, to serve particular purposes, additional embodiments within the scope of the present invention may incorporate combinations of different cross-sectional rim profiles in different segments along the perimeter of the rim. For example, in one embodiment, the rim includes one or more rim segments with an outer rim portion shaped to a substantially round cross-section, while retaining the configuration of the inner portion of the rim to provide an attachment site and protect the edge of the dome. This segment or segments can be placed at sites where the device may be particularly prone to contact the penis during intercourse, thus beneficially maximizing the radius of curvature of potential contact points between the rim and penis, and thereby improving comfort. Portions of the rim of the intravaginal device most likely to contact the penis are those portions of the rim that lie along the midline of the vagina during wear, and, in particular, the portion of the rim closest to the vaginal introitus. Thus, one such rounded segment can be provided where it can be positioned substantially behind the pubic bone.

Alternatively at least two rounded segments can be provided. The embodiment illustrated in FIG. 6 includes a rim divided into four segments having different cross-sectional profiles. As illustrated in inset A, the lateral segments 27a and 27b include an outer portion of the rim characterized by a profile substantially similar to the profile illustrated in FIG. 5. As illustrated in inset B, the midline segments 28a and 28b include an outer portion of the rim characterized by a substantially rounded cross-sectional profile. The rim profile may include a recessed inner portion as previously described for other embodiments. In use, at least one of the midline rim segments 28a can be positioned substantially behind the pubic bone, and the other segment 28b substantially within the posterior fornix.

Other embodiments can include modified segments of the rim cross-sectional shape with reduced rim cross-sectional dimensions at one or more sites. In one embodiment, the rounded outer portion of the rim may include a smaller cross-sectional dimension. This creates two hinge-like portions along the rim due to an increased flexibility associated with reduced cross-sectional portions along the rim dimension of these segments. These flexible segments can aid in folding the device during compression for insertion.

In one embodiment a midline segment may be tipped upward slightly out of the plane of the rest of the rim. This upwardly angled midline segment can be positioned substantially behind the pubic bone during wear. The upward tilt advantageously can aid in positioning that portion of the device further behind the pubic bone, and can separate it further from contact with the penis during intercourse. Other variations in the cross-sectional shape of the rim or of one or more segments of the rim can be envisioned within the scope of the present invention, so long as the rim segments incorporate the recessed inner rim portion in such a fashion as to create a protected attachment site for a separate dome piece.

Figure 7:
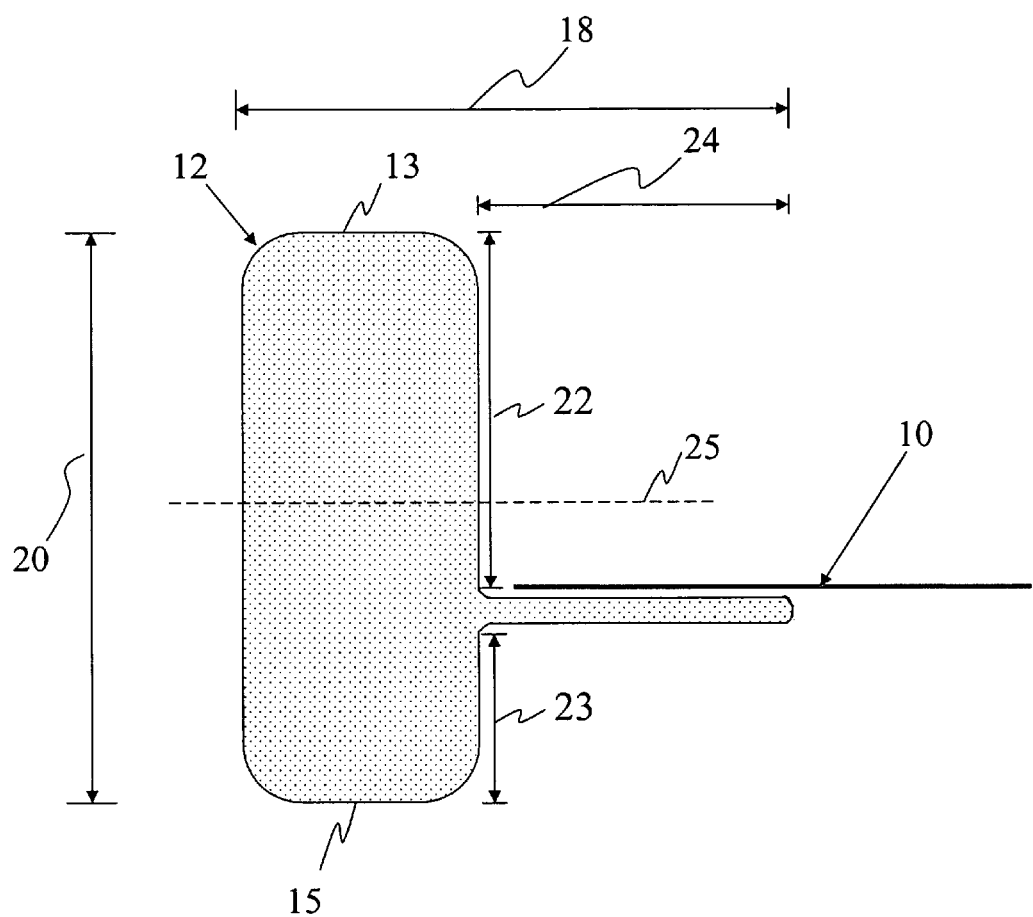
FIG. 7 is a cross-section of a portion of a rim and dome piece of an intravaginal device illustrating attachment of the dome piece within a recess in the rim of one embodiment of the present invention.

FIG. 7 illustrates another embodiment of the present invention including opposing recesses associated with the inner portion of the rim. The recesses can be positioned opposite one another in an asymmetrical fashion along the inner portion of the rim to define a dome attachment site at a position away from a substantially vertical center 25 of the rim. To this end, the vertical extent or depth of the recesses in the inner portion of the rim may be different with one recess 22 being deeper than the other recess 23, resulting in the attachment site along the inner portion of the rim being located asymmetrically at a position away from a central position 25 between a top portion 13 of the rim and a bottom portion 15 of the rim.

Although equivalently dimensioned and symmetrically positioned recesses of the inner portion of the rim are advantageous in avoiding the need for orientation steps in manufacture and insertion as described above, there are also advantages for embodiments with asymmetrical recesses of the inner portion of the rim. For example, different dimensions and asymmetric positioning of the recesses of the inner portion of the rim may change the degree to which the device bows when compressed. It should be appreciated that slight downward bowing can be advantageous since this folded configuration can help the leading edge of the rim pass easily below the cervix when the device is being inserted into the vagina. Moreover, asymmetrical recesses can form an inner rim portion of the rim that is oriented toward the bottom of the rim and, thereby, further improve access to the inner portion of the rim during retrieval from the vagina.

Figure 8:
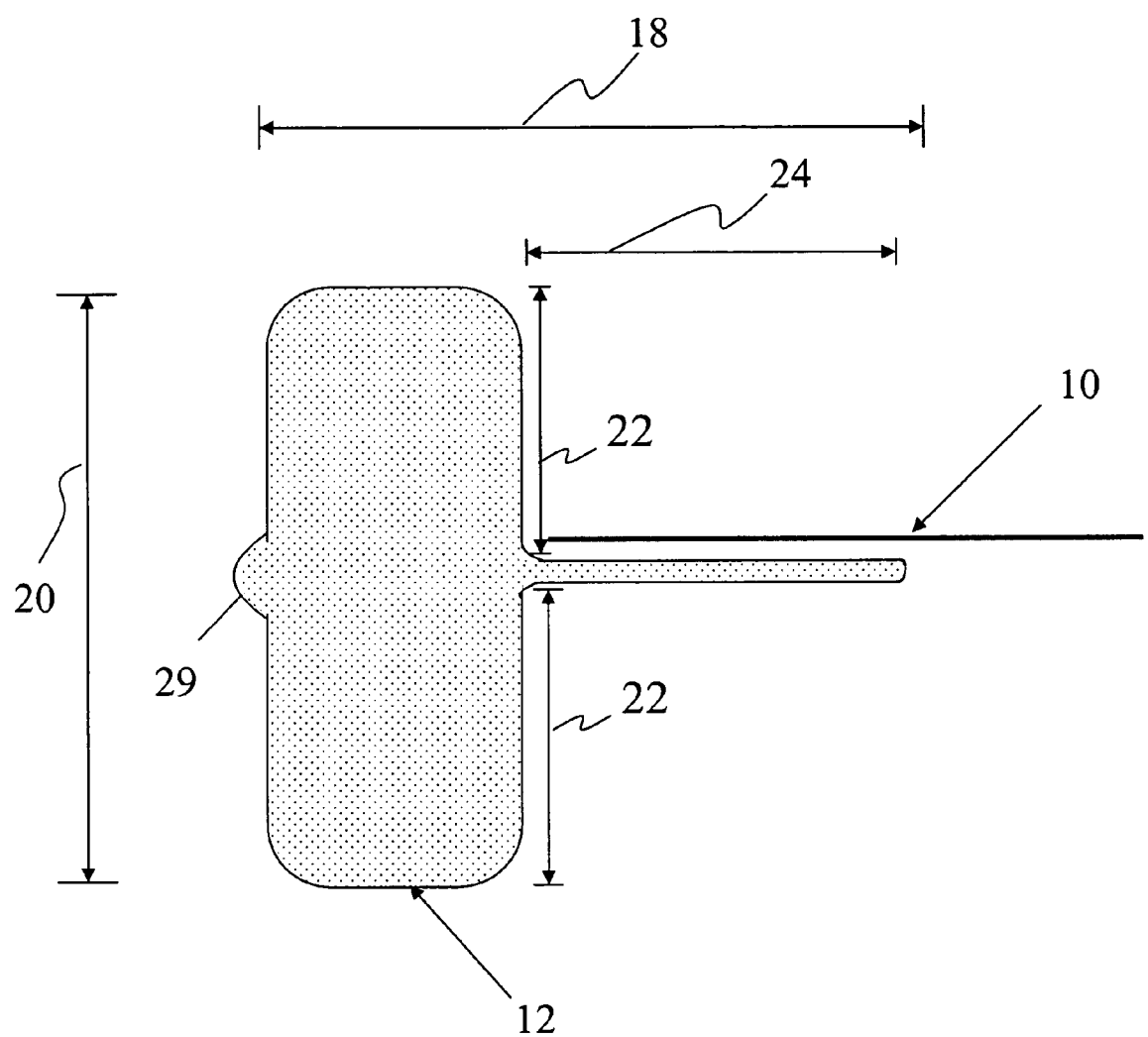
FIG. 8 is a cross-section of a portion of a rim and dome piece of an intravaginal device illustrating attachment of the dome piece within a recess in the rim of one embodiment of the present invention.
Figure 9:
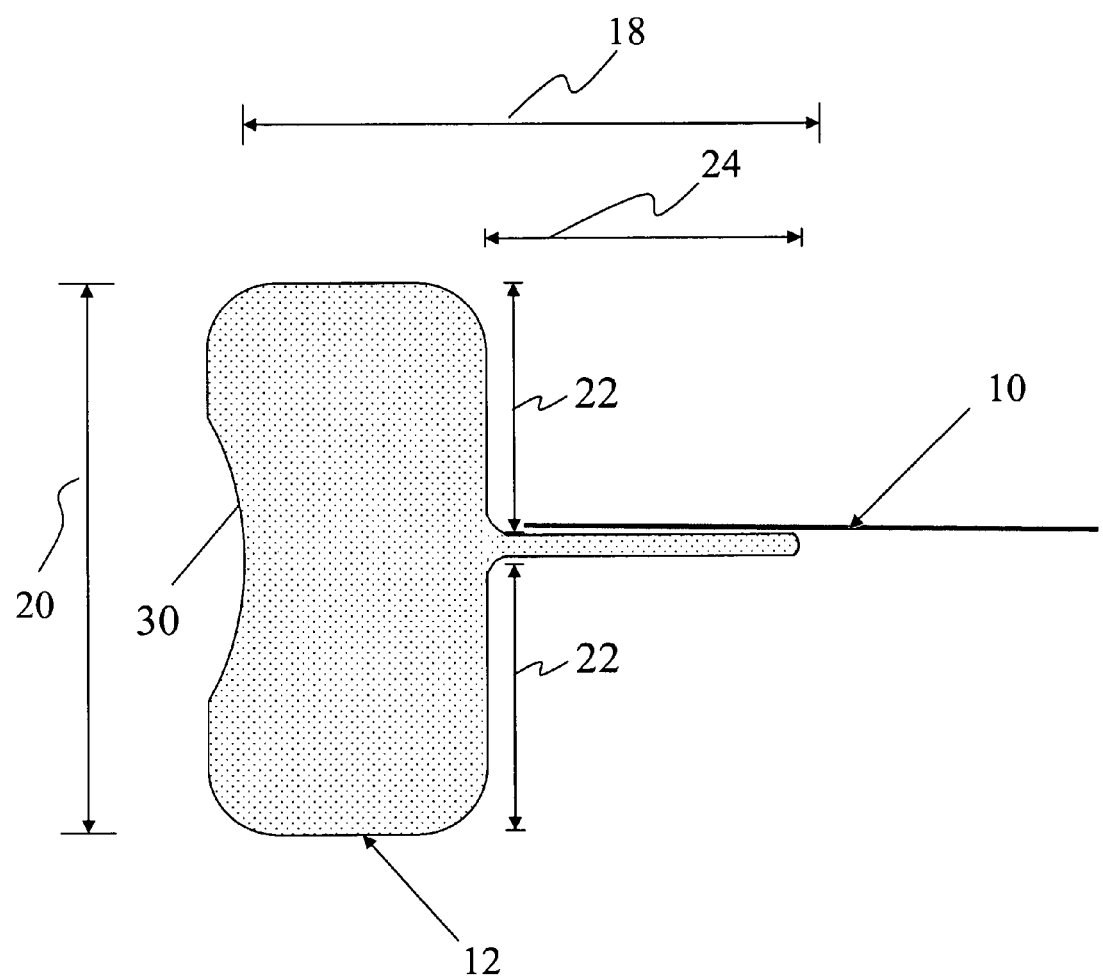
FIG. 9 is a cross-section of a portion of a rim and dome piece of an intravaginal device illustrating attachment of the dome piece within a recess in the rim of one embodiment of the present invention.
Figure 10:
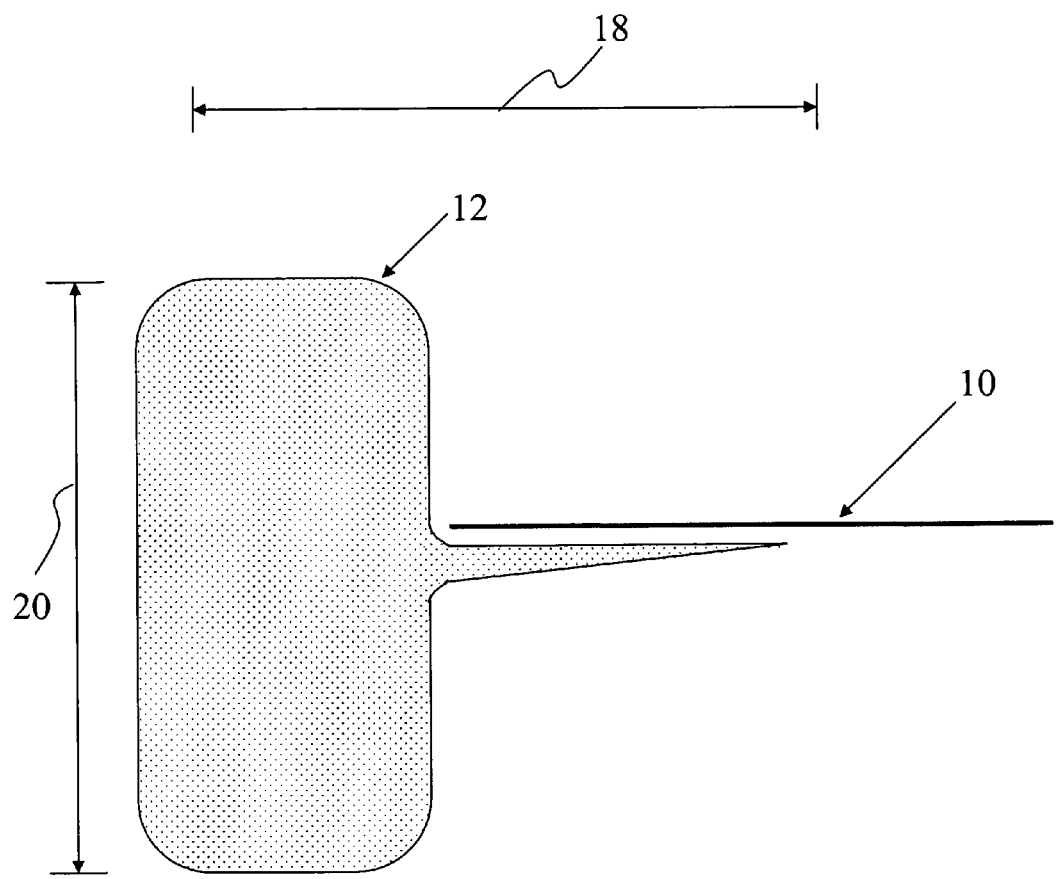
FIG. 10 is a cross-sectional view of a portion of a rim and dome piece of an intravaginal device illustrating attachment of the dome piece within a recess in the rim of one embodiment of the present invention.

Other features of the rim design of the present invention may include providing a more secure gripping surface on the outer surface of the rim. For example, in one embodiment, the outer rim surface is shaped to provide at least one outward projecting bead 29, as illustrated in FIG. 8, or, in another embodiment, at least one groove 30, as illustrated in FIG. 9. Other features to enhance the grip on the outer rim surface may include, but are not limited to, multiple beads and/or grooves, cross-hatching, or any other suitably shaped or textured surface which provides a more secure grip when the rim is held between the fingers for compression and insertion and/or contributes to maintaining the position of the device in the vagina. It should be appreciated that a secure grip is advantageous, since intravaginal devices are often used with lubricating gels or creams that may contain at least one active ingredient or any other beneficial agent such as spermicides, antivirals, antibacterials, antifungals, vaccines, hormones etc. The lubricating nature of these gels or creams makes the rim slippery; thus, a gripping feature is particularly beneficial.

It should be appreciated that other shapes or conformations of recesses can be associated with the inner portion of the rim to form a suitable attachment site for the dome piece and to achieve additional benefits. For example, the shape of the recesses that define the shape of the inner portion of the rim can be rounded or curved. In one embodiment illustrated in FIG. 10, a recess can form an inner portion of the rim that is tapered through to a substantially horizontal inner portion of the rim. The shape of the recesses may define an inner portion of the rim that approaches the thickness and compliance of the dome piece material. Advantages of this tapered shape include maintaining the strength of the inner portion of rim while producing a substantially thin and, therefore, soft or flexible inward-facing edge in order to avoid any harsh impingement on the cervix which will be located within the perimeter of the rim during wear within the vagina.

The rims of the present invention can be made by injection molding of thermoplastics. Molding of polymers such as silicone into the rim profiles of the present invention can be used wherein the polymerization and/or cross-linking occurs in situ within the mold. Alternatively, the rim profile can be formed by extrusion from a die and cut to length. The two ends of the rim may be joined to form a closed, substantially circular or substantially oval shape, and fused by any suitable means such as thermowelding, ultrasonic welding, radiofrequency welding, use of a suitable adhesive or any other suitable method of securing together the ends of the rim.

Materials suitable for fabrication of intravaginal devices of the present invention include, without limitation, various thermoplastic polyurethanes, ethylene vinyl acetate, polyethylene, styrene-butadiene-styrene, styrene-ethylene/butylene-styrene, and silicone. Mixtures of two or more of these materials may also be employed. Different materials, or different hardness grades of the same materials can be used for the separate dome and rim pieces. For example, if the attachment method includes a step to heat and soften the dome and rim surfaces to be bonded, it is advantageous that dome and rim be made of the same material. If the materials of the dome and rim are not the same, each may contain at least some percentage of a material present in the other component in order to enhance the success of bonding by a heating method. It is generally advantageous for the dome material to be chosen for softness and drape, and for the rim material to be chosen for greater stiffness to provide an adequate outward holding force.

Figure 11A:
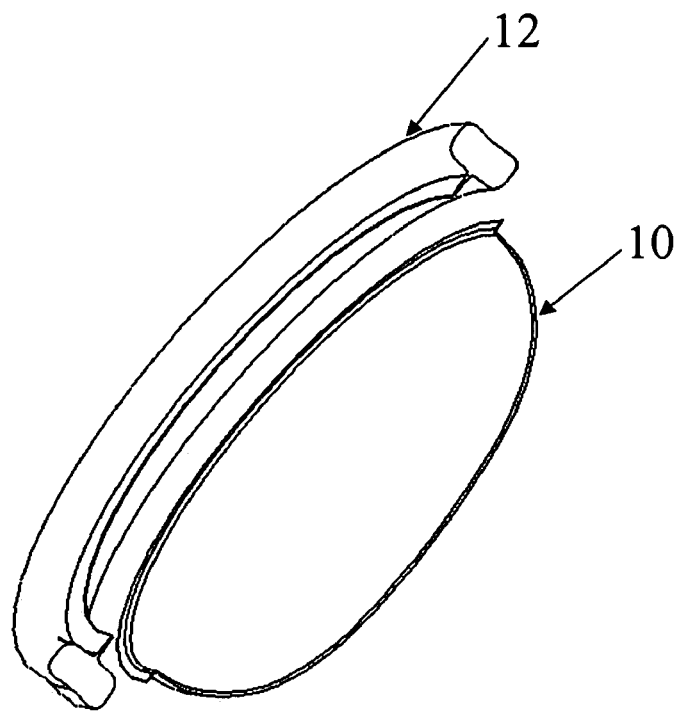
FIG. 11A is a cross-sectional perspective exploded view of the intravaginal device of one embodiment of the present invention with an attached and formed dome.
Figure 11B:
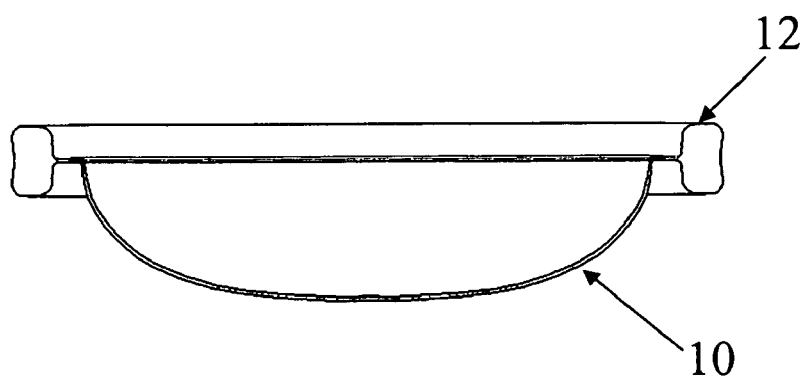
FIG. 11B is a cross-sectional view of an intravaginal device of one embodiment of the present invention with an attached and formed dome.

The rim designs of the present invention can be combined with dome pieces of any suitable shape or configuration. For example, a simple, substantially hemispheric shape of conventional diaphragms can be combined with the rim designs of the present invention as illustrated in FIGS. 11A and 11B. Other dome shapes can be combined with the rim designs of the present invention including, in one embodiment, the sombrero-shaped dome discussed above and illustrated in FIGS. 12A and 12B. In one embodiment, the dome film is shaped to its desired shape by vacuum thermoforming or other methods known in the art once the dome piece is attached to the dome attachment site 16 of the rim. In another embodiment, the dome film is shaped prior to being attached to the dome attachment site 16 of the rim. Moreover, if shaped prior to being attached, the dome film can be shaped by any suitable method and not restricted to thermoforming from a flat sheet of film.

Figure 13A:
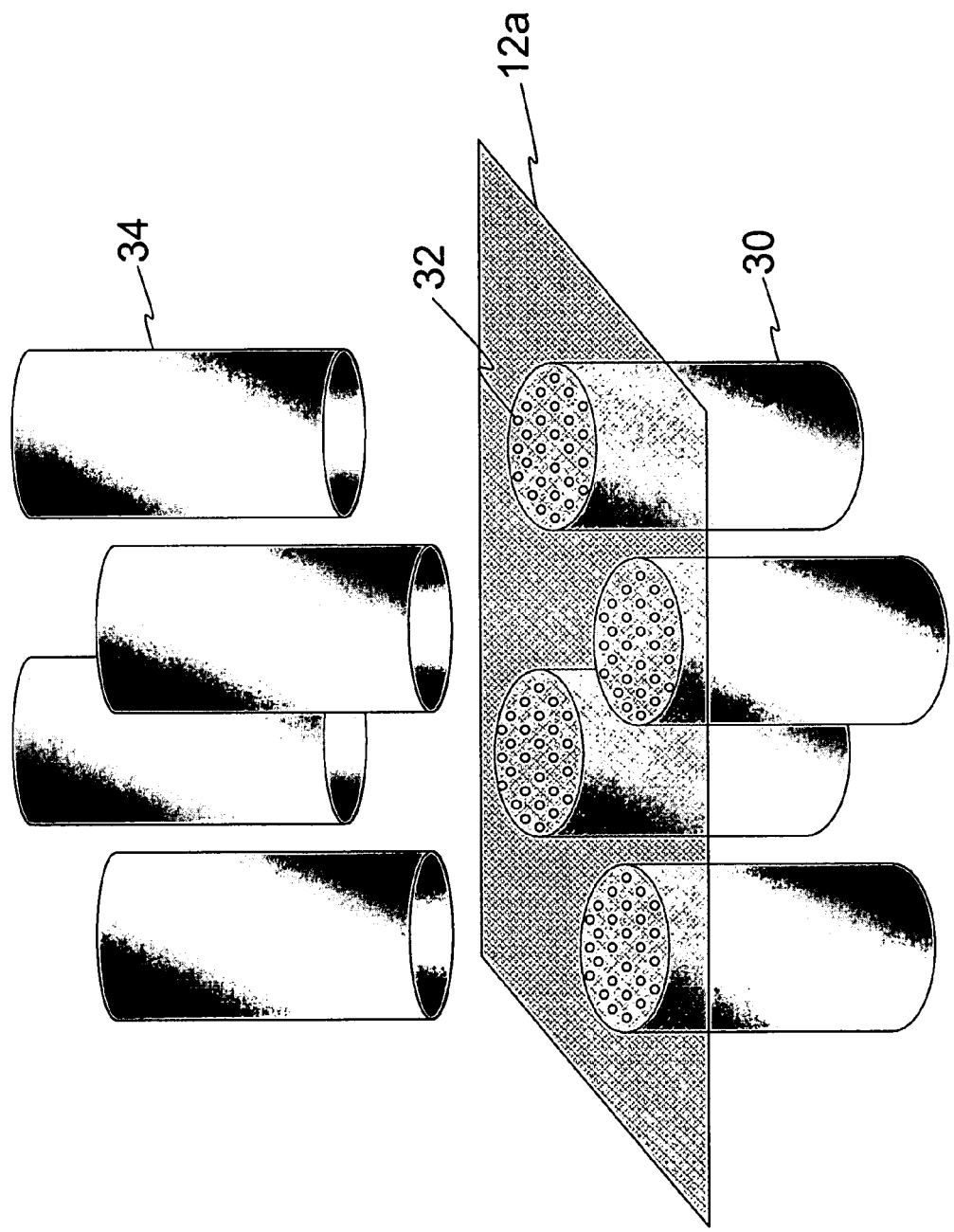
FIG. 13A is a perspective view of a portion of an apparatus used to manufacture dome pieces according to the method of one embodiment of the present invention.

Referring to FIGS. 13A and B, an embodiment of the present invention includes an alternative method of cutting, positioning, holding in place, and attaching a plurality of rims and dome pieces that is suitable for high-volume manufacturing. The method includes placing a sheet of dome material film 12*a* on a holding surface of each of an array of holding pedestals 30. The holding surfaces of the holding pedestals may be sized to the dimensions necessary for subsequent formation of the dome piece 12 of the intravaginal device. The dome material film 12*a* can be reversibly held or affixed to the holding surface of each of the holding pedestals 30 by applying vacuum to the film through a plurality of channels 32 emerging through the holding surface of the holding pedestals 30.

The method can further include providing a matching set of at least partially hollow cutting cylinders 34. Each of the cutting cylinders 34 may be positioned opposite one of the holding pedestals 30 and each of the cutting cylinders 34 may include inside dimensions substantially equal and corresponding to outside dimensions of the holding surface of the holding pedestal 30. The cutting cylinders 34 can be pressed down over the film 12*a* beyond the holding surfaces of the holding pedestals 30 into a bypass cutting position. Accordingly, the cutting cylinders 34 can function as bypass cutters, trimming the film into a set of disc-shaped dome pieces 12 having a diameter substantially equal to the diameter of the holding surface of the holding pedestal. In one embodiment, heat can be applied to the cutting cylinders 34 to enhance the cutting action achieved. After retracting or removing the cutting cylinders from the bypass cutting position, the web of film 12*a* from which the dome pieces 12 have been cut is removed. It will be appreciated that the orientation of the holding pedestals and cutting cylinders described above can be altered as needed for efficient manufacture.

Figure 13B:
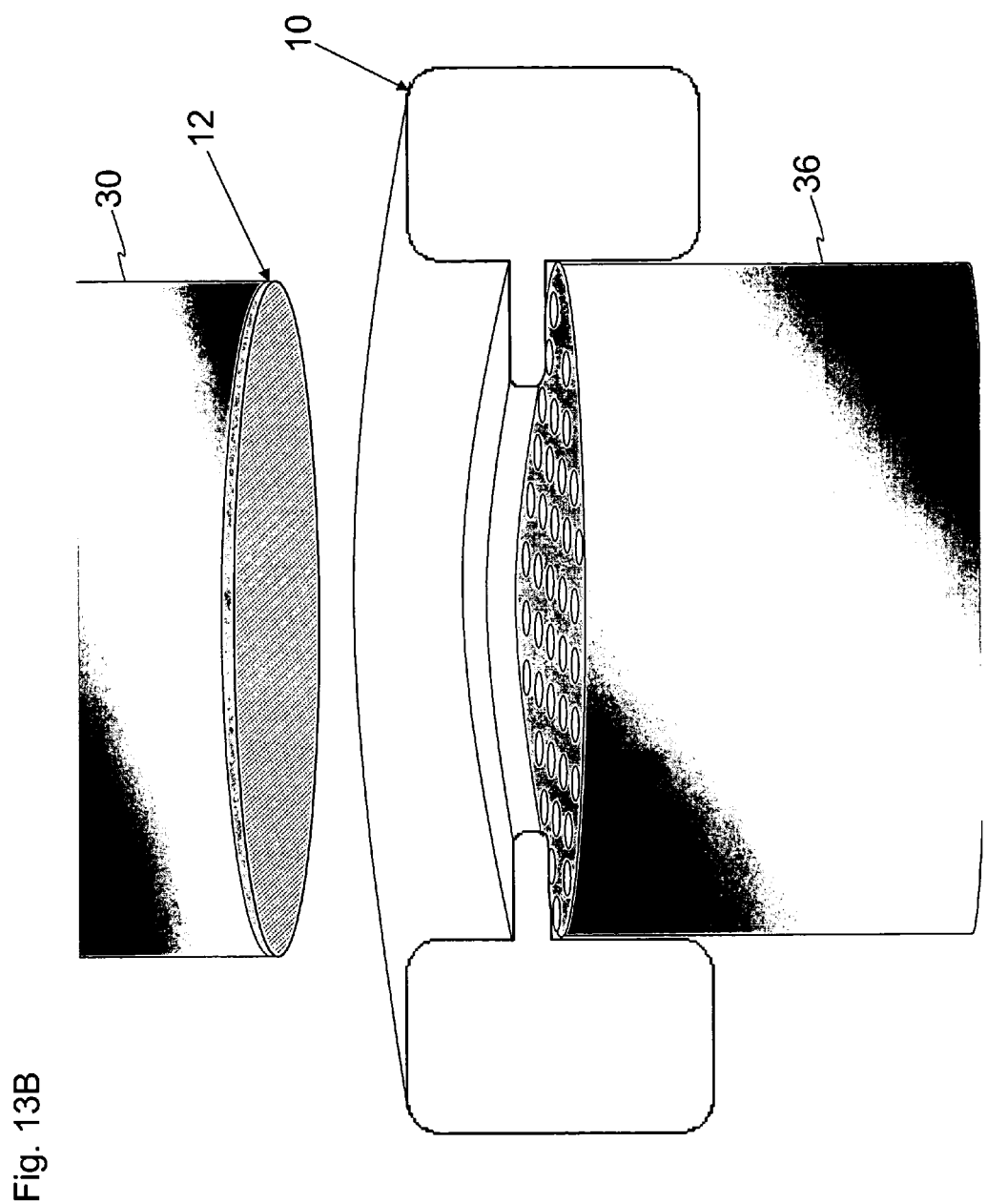
FIG. 13B is a cross-sectional perspective view of a single operational component of an apparatus used to attach a dome piece to a rim piece according to the method of one embodiment of the present invention.

As illustrated in FIG. 13B, in one embodiment, the rim 10 to which a dome piece 12 is to be attached can be placed on a rim support pedestal 36. Each rim support pedestal 36 may be adapted to support the inner portion of a rim 10 to which a dome piece 12 is to be attached. In an embodiment, a plurality of rim support pedestals 36 are provided. These rim support pedestals 36 can be arranged in an array configured to match an array of holding pedestals 30 such that each holding pedestal is positioned opposite one of the rim support pedestals. In one embodiment, each of the rim support pedestals 36 is supplied with channels 32 on at least a perimeter of a support surface through which vacuum can be applied to hold the rim piece 10 in place. In one embodiment, each of the rim support pedestals 36 is supplied with channels 32 in a substantially central portion of its support surface through which vacuum can be applied to hold the dome piece 12 in place when positioned for attachment to the rim piece 10. The array of holding pedestals 30 and their vacuum-held dome pieces 12 may be inverted, and operably positioned to insert each of the plurality of dome pieces 12 into a recess of each of the plurality of rim pieces 10 operably positioned on the rim support pedestal 38 to receive the dome piece 12. Vacuum may be applied to the central portion of the support surface of the rim support pedestals 38 to hold the dome piece in a precise position against the inner portion of the rim 10 for attachment to the rim. Upon suitable positioning of the dome piece within the recess of the rim, vacuum from the holding pedestals 30 may be discontinued, and the holding pedestals 30 removed or retracted to a retracted position leaving each of the dome pieces 12 in a position to be attached to the rim pieces 10 supported by the rim support pedestals 36.

In an embodiment of the present invention the subsequent dome attachment step is by thermowelding with an array of weld tools distinct from the array of holding pedestals. In another embodiment, welding tools are incorporated into the holding pedestals by providing a heating element along the perimeter of their holding surfaces.

The dome film can be manufactured by any suitable means. In an embodiment including a dome piece comprising a flat film attached to a rim of the present invention with subsequent steps to form the dome, the film can be manufactured by calendaring, blow molding or extrusion. The dome material can be any desired thickness, although, as described above, it is advantageous that the completed dome be relatively thin, preferably less than about 1 mm, and more preferably less than about 0.2 mm in thickness. To retain adequate strength, and to reduce the chance that holes will be created during manufacture, it is generally preferable that the dome have a minimal thickness of about 0.05 mm.

Other methods for creating and attaching a dome to the rims of FIGS. 5-12 include a polymer/solvent dipping or spraying method. The dipping method includes attaching the rim to a mandrel. The mandrel is dipped in a polymer/solvent mixture so that the mixture coats the mandrel and contacts the inner portion of the rim. The solvent is subsequently removed by evaporation.

In polymer/solvent-based methods, the thin inner portion of the above-described rims can be useful to provide an efficient seal to the mandrel. An effective seal to the mandrel is preferable to prevent the polymer/solvent mixture from moving higher on the mandrel than is desirable, and from being deposited at sites other than those intended. The rims of the present invention, such as those described in FIGS. 5-12, are well suited for this process, since the thicknesses of the inner portions of the rims described in FIGS. 5-12 can be made sufficiently thin to make these inner portions compliant and flexible. To achieve sufficient compliance to produce an effective seal to the mandrel, it is advantageous that the thickness of the inner portion is between about 1 and about 0.01 mm, and more advantageously between about 0.5 and about 0.1 mm. It should be appreciated that the thickness of the inner portion of the rim necessary to achieve sufficient compliance may vary from these disclosed measurements, depending on the material(s) of the rim. As discussed above, the greater stiffness of the inner portion of the rim in comparison to the attached dome enables the inner portion of the rim to serve as a handle that assists positioning in the vagina and removal from the vagina, just as with a dome film attached by thermowelding or other means of attaching a preformed dome film.

An additional benefit of rim designs of the present invention includes a more favorable compatibility with common polymer/solvent methods of dome fabrication: the inner portion of the rim can be positioned to selectively or exclusively contact the solvent/polymer mixture without contacting the outer portion of the rim. To this end, the mandrel may deflect the free edge of the inner portion of the rim to allow the inner portion of the rim to project downward, beyond the lower edge of the outer portion of the rim and toward a solvent/polymer bath or a spray-head. To further position the rim in an advantageous position for attachment of the dome piece, the lower aspect of the outer portion of the rim can be twisted upward and outward.

Certain embodiments of the present invention are helpful to further enable exclusive contact of the inner portion of the rim with the solvent/polymer mixture. One embodiment arranges the recesses in the rim to position the dome attachment site on the inner portion of the rim in closer proximity to a peripheral edge of the rim as it is held for dipping. This allows the dome attachment site to be optimally positioned to enable sufficient downward deflection upon contact with the mandrel. In addition, the recesses in the rim may define a width of the inner portion of the rim that enables sufficient downward deflection upon contact with the mandrel. Such a width can be advantageously made between about 2 and about 6 mm, and more advantageously between about 3 and about 4 mm.

Dipping methods to create thin films of latex, polyurethane, or other polymers, may also be employed to create the dome. For example, solvents that are useful for polyurethane dip molding include tetrahydrofuran, dimethyl acetamide N-methylpyrrolidone, and dimethyl formamide. Additional agents can be added such as weak solvents or non-solvents of polyurethane to adjust viscosity and enhance removal of solvents after dipping. These agents include aliphatic alcohols, aliphatic amines, aliphatic and aromatic hydrocarbons. Polymeric concentrations in the polymer/solvent mixture can be advantageously from about 5 to about 10% by weight, and the viscosity of the polymer/solvent mixture can be advantageously controlled between about 500 and about 1000 cP.

The mandrel and attached rim can be slowly lowered into the dip solution, allowed to remain there for a few seconds, and slowly removed. The solvents can be allowed to evaporate. The mandrel can be rotated to control the thickness of various portions of the dome through gravity-induced movement of the dip solution before its solvent evaporates. Heat, vacuum, and solvent recovery steps may be included in the solvent evaporation process to speed drying, and to reduce material costs and environmental pollution. Other suitable methods for the dip molding of latex films and other polymer films are known in the art, and can be chosen to fabricate domes by polymer/solvent dipping with appropriate adjustments of polymer concentration, solvents, and evaporation conditions.

Alternatively, the polymer/solvent mixture can be sprayed onto the rim and mandrel assembly.

An advantage of attaching the solvent-dipped or sprayed dome to the inner portions of the rims of the present invention, includes the removal of solvent from the rim during the solvent evaporation stage than if the solvent had contacted and penetrated into a thicker portion of the rim.

EXAMPLE 1

Figure 1:
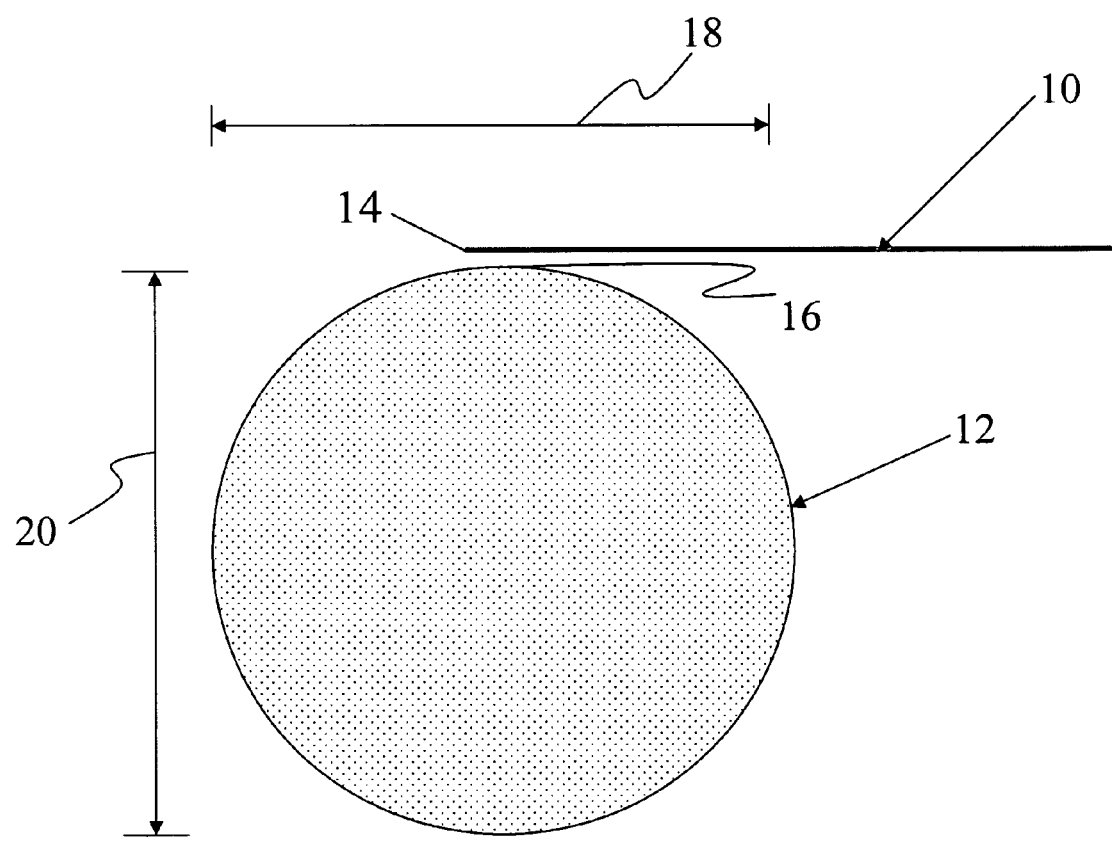
FIG. 1 is a cross-section of a portion of a rim and dome piece of an intravaginal device, with the dome piece positioned above the rim in preparation for attachment at a site on the rim where the dome piece is conventionally attached.

A rim with a generally round cross-section, as illustrated in FIG. 1, is fabricated from aromatic polyurethane by injection molding. Thermoplastic polyurethane film of 0.0075-inch (0.19 mm) thickness is welded to the top surface of the rim using a heated welding tool. During the application of heat and pressure, the excess film is pulled upward and away from the weld line, parting the film at the melted edge of the weld line. The attached flat film is then heated with hot air, and vacuum thermoformed into the desired dome shape. The outer edge of the weld line is found to be rough to the touch. This roughness is fully exposed, accessible, and easily felt.

When the rim is compressed between the thumb and fingers, as in preparation for insertion, the rim contorts into undesirable configurations. First, as seen from the side view, it bows dramatically into a pronounced "C" shape. In addition, as seen from above, it twists into a twisted "figure-8". Either of these configurations makes it difficult to hold and to maintain control of the compressed rim, making insertion into the vagina more difficult. Both of these inconvenient contortions are also commonly observed with traditional contraceptive diaphragms.

A variant of the round rim is molded with flat inner surfaces at the point of compression, allowing more stable mating of the inner rim surfaces as they are pressed together. This configuration does not significantly improve the bow and twist problems described above. An additional variant with a tongue and groove interlock feature machined into the flat region on the inside of the rim is fabricated, but, again, this does not significantly reduce the bowing or twisting.

EXAMPLE 2

A rim 12 with a cross-sectional configuration as shown in FIG. 8 that includes an outward facing bead on the outer surface of the rim is molded of thermoplastic polyurethane. This design is an example of the general strategy illustrated in FIG. 5, wherein the inner portion of the rim is sufficiently recessed such that the inner portion of the rim forms an attachment site for the film, is positioned substantially at the vertical center between a top portion and a bottom portion of the rim to make the rim essentially symmetrical for simplicity in manufacture and for convenience during insertion. A dome piece made from a pre-cut disk of 0.0075-inch (0.19 mm) thick polyurethane film is laid over the inner portion of the rim and attached by thermowelding. The flat film is shaped into a dome configuration (FIG. 11) using vacuum thermoforming, resulting in a final dome film thickness of 0.002 to 0.005 inch (0.05 mm to 0.13 mm).

The outer edge of the film is found to be highly and advantageously inaccessible and protected due to its location within the deep recess in the rim. The non-recessed outer portion of the rim prevents contact with any roughness of the cut edge of the dome film. The tendency of the rim to bow or twist upon compression is greatly reduced in comparison to the device of Example 1. The bead on the external surface of the rim provides good security in holding the rim for compression and insertion. The rim is symmetrical and can be positioned with either side up during the dome attachment step of manufacture. Similarly, the completed device is essentially symmetrical, particularly where the dome is formed as in FIG. 11 as a compliant hemispheric shape. The completed device can be inserted with either side up, making insertion more convenient. Finally, the inner portion of the rim can be securely engaged by the index finger for removal from the vagina.

EXAMPLE 3

A rim as shown in FIG. 9 is molded of thermoplastic polyurethane. The design is again similar to that illustrated in FIG. 5, with the inner portion of the rim being deeply recessed symmetrically at its top and bottom. The outer surface of the rim contains a groove as a grip feature rather than the bead of Example 2. A dome piece made from a pre-cut disk of polyurethane film is welded to the inner portion of the rim (at the floor of the recess) by thermowelding. The attached flat film is then shaped into a dome configuration (FIG. 12) using vacuum thermoforming.

As in Example 2, the edge of the film attached to the rim of Example 3 is advantageously protected, due to its location deep within the recess and away from the external surface of the rim. The higher vertical profile of the outer portion of the rim prevents contact with any roughness of the cut edge of the dome film. The finished device demonstrates much less tendency to twist or bow compared to the device in Example 1. The outward facing groove provides for secure gripping of the device while compressing it for insertion. Lastly, the inner portion of the rim is easily engaged by the index finger as for positioning within or removal from the vagina.

It will be understood that although this and the previous examples employ fully elastomeric rims, rims that incorporate metal springs are also within the scope of the present invention. Likewise, intravaginal devices with rims providing the improved dome attachment features described in the present invention can also serve additional or alternative functions such as the delivery of beneficial agents, and collection and removal of substances from the vagina.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An intravaginal device, comprising:
   a dome piece including an outer edge defined by a first dome piece surface and a second dome piece surface; and
   a rim piece including an inner portion, said inner portion including two opposed recesses configured to form a first inner portion surface opposite a second inner portion surface, wherein said first inner portion surface includes an attachment site in contact with said first dome piece surface, and wherein said second dome piece surface is not in contact with said rim piece.

2. The device of claim 1, wherein a cross-sectional width of the rim piece of said device is greater than or equal to a cross-sectional height of said rim piece.

3. The device of claim 1, wherein at least one of said recesses includes a depth at least as great as a thickness of said dome piece.

4. The device of claim 1, wherein the depth of at least one of the recesses is equal to at least one of the dimensions of at least one other recess.

5. The device of claim 1, wherein the depth of at least one recess is different than the depth of at least one other recess.

6. The device of claim 1, wherein the recesses associated with the inner portion of the rim piece define a thickness of said inner portion of said rim piece, wherein said thickness is substantially equivalent to the thickness of the dome piece.

7. The device of claim 1, wherein the recesses define a dome piece attachment site at a substantially central position along the inner portion of said rim piece.

8. The device of claim 1, wherein the dome piece is attached to the rim piece at a substantially central position between a top portion of said rim piece and a bottom portion of said rim piece.

9. The device of claim 1, wherein the dome piece is attached to the rim piece at a position away from a central position between a top portion of said rim piece and a bottom portion of said rim piece.

10. The device of claim 1, wherein the thickness of said inner portion of said rim piece is between about 0.01 millimeter and about 1 millimeter.

11. The device of claim 1, wherein the inner portion of said rim piece is adapted to function as a handle to position the device within a vagina and remove the device from the vagina.

12. The device of claim 1, wherein an outer portion of said rim piece includes one or more outwardly projecting circumferential beads.

13. The device of claim 1, wherein an outer portion of said rim piece includes one or more circumferential grooves.

14. The device of claim 1, wherein the dome piece is attached to the rim piece by an attachment method selected from the group consisting of: thermowelding, ultrasonic welding, radiofrequency welding, solvent welding, and adhesive attachment.

15. A method of forming an elastomeric dome piece of the intravaginal device of claim 1, which includes, after attaching said dome piece to said rim piece, softening the dome piece by heating, and drawing the dome piece by vacuum into a mold, wherein the mold is shaped to a desired dome piece shape.

16. The device of claim 1, wherein the inner portion of the rim piece includes a tapered shape.

17. The device of claim 1, wherein the dome piece includes a thickness of less than about 1 mm.

18. The device of claim 17, wherein the thickness of the outer edge of said dome piece is less than about 1 mm.

19. A method of removing substances from the vagina comprising:
operably positioning in the vagina of an individual in need thereof an intravaginal device, said device including a rim piece having an inner portion and a dome piece including an outer edge defined by a first dome piece surface and a second dome piece surface, wherein said rim piece includes at least two recesses associated with said inner portion, said recesses opposing one another to define a first inner portion surface opposite a second inner portion surface, wherein said first inner portion surface includes an attachment site in contact with said first dome piece surface, and wherein said second dome piece surface is not in contact with said rim piece; and
removing said intravaginal device and said substances from the vagina.

20. A method of applying a substance to the vagina of an individual comprising:
applying a substance to an intravaginal device, said device including a rim piece having an inner portion and a dome piece including an outer edge defined by a first dome piece surface and a second dome piece surface, wherein said rim piece includes at least two recesses associated with said inner portion, said recesses opposing one another to define a first inner portion surface opposite a second inner portion surface, wherein said inner portion surface includes an attachment site in contact with said first dome piece surface, and wherein said second dome piece surface is not in contact with said rim piece; and
operably positioning said intravaginal device in the vagina of the individual.

21. A method of contraception comprising:
operably positioning an intravaginal device in the vagina of an individual in need thereof prior to sexual intercourse, said device including a rim piece having an inner portion and a dome piece including an outer edge defined by a first dome piece surface and a second dome piece surface, wherein said rim piece includes at least two recesses associated with said inner portion, said recesses opposing one another to define a first inner portion surface opposite a second inner portion surface, wherein said first inner portion surface includes an attachment site in contact with said first dome piece surface, and wherein said second dome piece surface is not in contact with said rim piece.

22. A method of preventing transmission of infection caused by secretions comprising:
operably positioning an intravaginal device in the vagina of an individual in need thereof, said device including a rim piece having an inner portion and a dome piece including an outer edge defined by a first dome piece surface and a second dome piece surface, wherein said rim piece includes at least two recesses associated with said inner portion, said recesses opposing one another to define a first inner portion surface opposite a second inner portion surface, wherein said first inner portion surface includes an attachment site in contact with said first dome piece surface, and wherein said second dome piece surface is not in contact with said rim piece; and
removing said secretions from the vagina with said intravaginal device.

* * * * *